United States Patent [19]

Michelson

[11] Patent Number: 4,973,321
[45] Date of Patent: Nov. 27, 1990

[54] CANNULA FOR AN ARTHROSCOPE

[76] Inventor: Gary K. Michelson, 438 Sherman Canal, Venice, Calif. 90291

[21] Appl. No.: 324,727

[22] Filed: Mar. 17, 1989

[51] Int. Cl.⁵ ............................................. A61M 25/00
[52] U.S. Cl. .......................................... 604/280; 128/4
[58] Field of Search ............... 604/280, 264, 265, 266, 604/281, 282; 128/348.1, 303.15, 303 R, 4

[56] References Cited

U.S. PATENT DOCUMENTS

| 4,717,379 | 1/1988 | Ekholmer | 604/280 |
| 4,840,623 | 6/1989 | Quackenbush | 128/348.1 |

Primary Examiner—John D. Yasko
Attorney, Agent, or Firm—Lewis Anten

[57] ABSTRACT

A tubular cannula having inwardly radially directed projections for closely supporting an arthroscopic viewing element is disclosed. The use of radially directed projections to support the arthroscopic viewing element permits the creation of an increased volumetric space between the inside wall of the cannula and the arthroscopic viewing element, thereby permitting an increased fluid flow during an operation using the device while at the same time increaseing the support for the arthroscope.

15 Claims, 2 Drawing Sheets

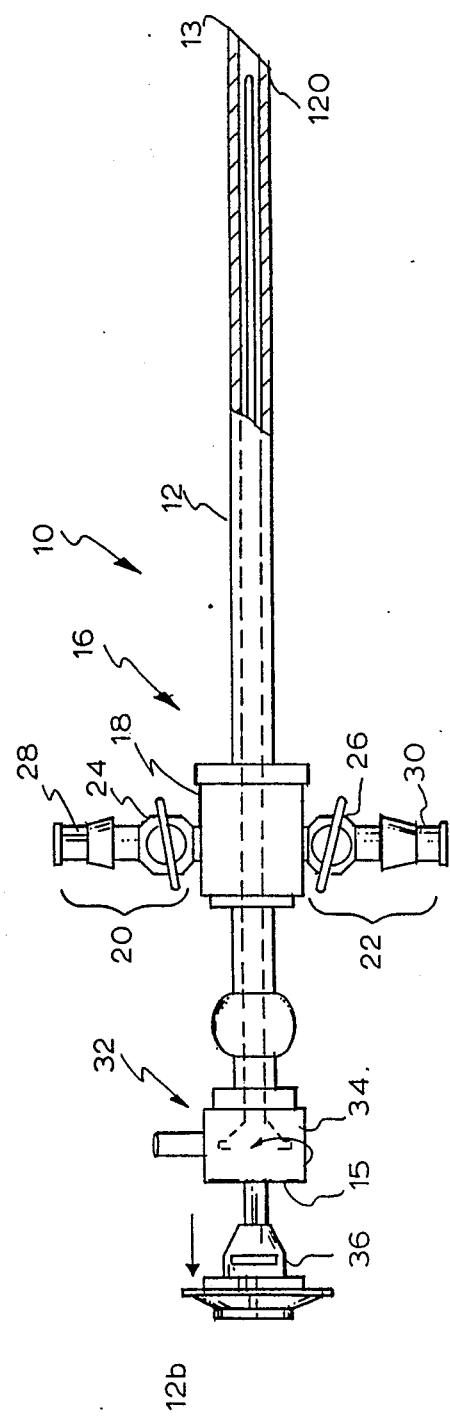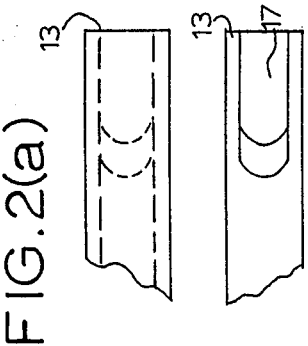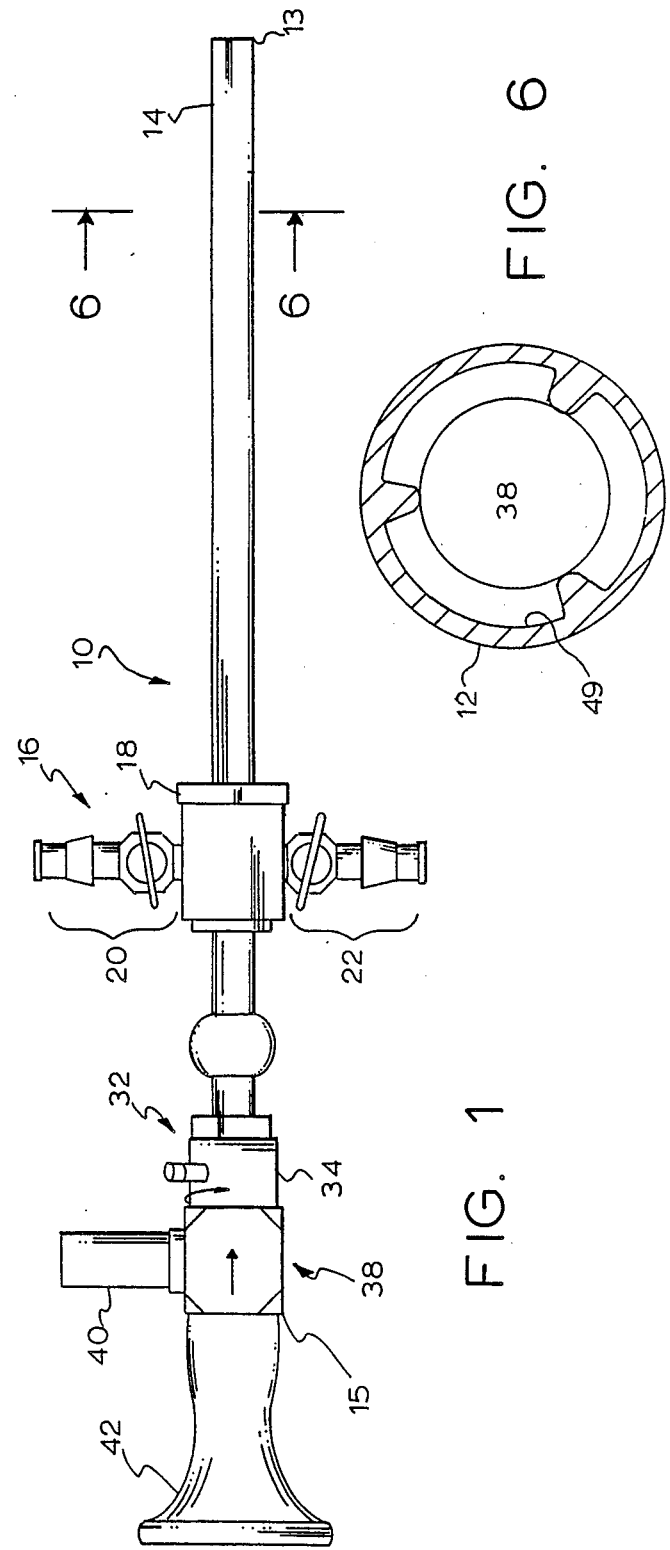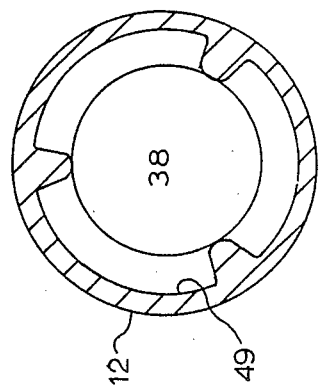

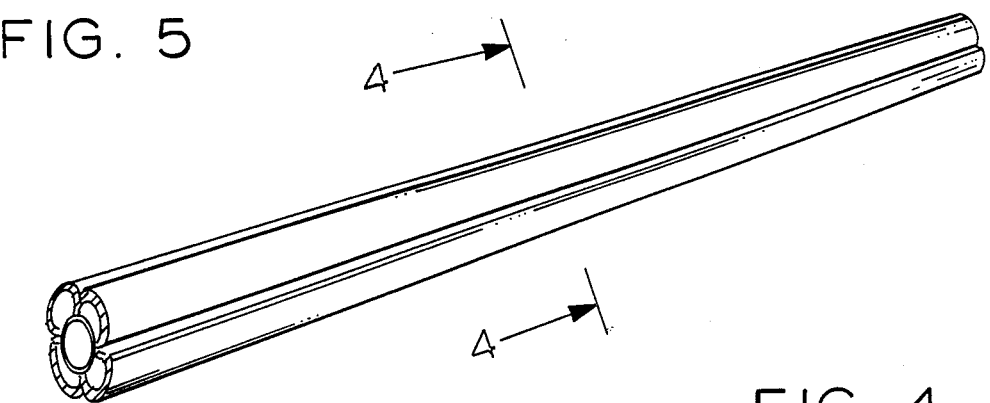
FIG. 5
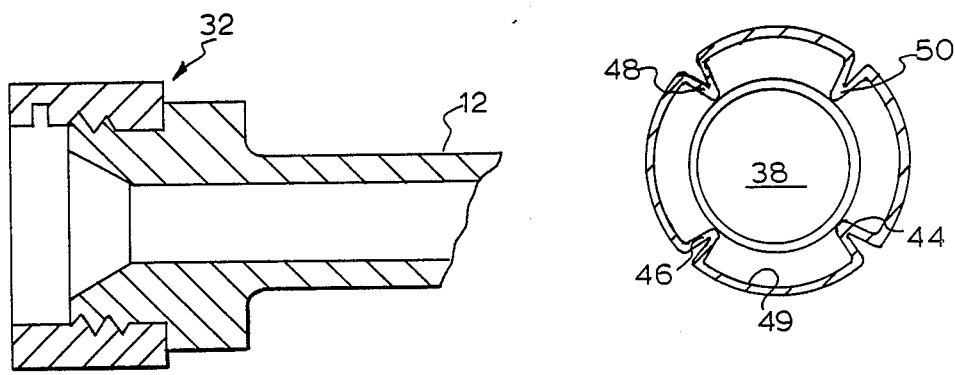
FIG. 3
FIG. 4
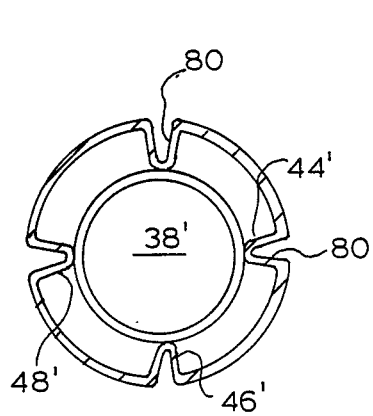
FIG. 8
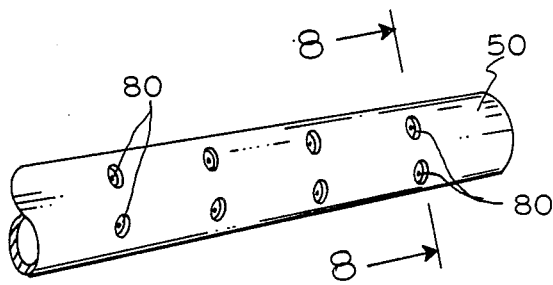
FIG. 7

CANNULA FOR AN ARTHROSCOPE

BACKGROUND

Endoscopes are slender light transmitting glass lined metal rods used during operations to permit the doctor to see within the site of the operation, such as during an arthroscopic procedure. Endoscopes designed and dimensioned for use in the joints of the body are referred to as arthroscopes. Since arthroscopes are very expensive, typically many thousands of dollars, and are very fragile, they are carefully protected by an outer cannula. A cannula is a tubular sleeve like member that closely surrounds the arthroscope, mitigating against breakage, during introduction into the wound or during use.

During an operation, it is necessary in order for the surgeon to see within the operating space for fluid to be introduced into the site of the operation to both inflate the site of the operation and to make sure that clear fluid is in the site. This is typically achieved by having an inlet at the proximate end of the cannula which forces sterile water through the space between the inside wall of the cannula and the outer wall of the arthroscope and into the wound. If the fluid becomes cloudy, then the inlet is closed and suction can be applied to an outlet at the proximate end to withdraw the cloudy fluid.

However, because of the close tolerances required to support the arthroscope, the volumetric space between the cannula wall and the arthroscope is very limited, and can not be arbitrarily increased. If too much clearance is provided, then the support to the arthroscope may be insufficient to prevent its breakage. Further, the size of the cannula can not be substantially increased due to the inability to maneuver a substantially larger instrument into the operation site. Thus, when substantial amounts of fluid must be introduced into the operation site and insufficient flow is obtainable through the arthroscope and cannula device, it is then necessary to introduce the fluid through additional incisions made into the site. While this is undesirable in any case, in some procedures, such as an arthroscopic procedure on the shoulder, the additional incisions could cause real damage to the rotator cuff. At the same time, the presence of additional tubes cause the procedure itself to be more difficult to perform. Thus, the design of the prior cannula represented a compromise between the desire to adequately support the arthroscope and the desire to have fluid flow.

SUMMARY OF THE INVENTION

The present invention relates to a cannula used with arthroscopes during surgery. More particularly, the cannula design permits an increased volumetric flow between the inside wall of the cannula and the outside wall of the arthroscopic viewing element, without substantially increasing the size of the cannula, while at the same time improving the support provided by the cannula to the arthroscopic element. This is achieved, in the preferred embodiment, by corrugating the cannula wall forming a series of inwardly directed radial projections or segments for providing increased support to the arthroscopic element. The use of the projections permits the use of a thinner cannula wall and an increased volumetric space for the flow of fluids in and out of the wound site. The increased flow reduces the number of instances where it is necessary to make a separate incision for the purpose of introducing fluid into the operation site.

OBJECTS OF THE INVENTION

It is an object of the present invention to provide an improved cannula for use with an arthroscope that is safer;

It is another object of the preset invention to provide an improved cannula for use with an arthroscope that permits increased fluid flow through the cannula;

It is still another object of the preset invention to provide an improved cannula for use with an arthroscope that provides increased support to the arthroscope;

It is another object of the preset invention to provide an improved cannula for use with an arthroscope that reduces the number of instances where additional incisions must be created;

It is another object of the preset invention to provide an improved cannula for use with an arthroscope that is stronger and reduces breakage of an arthroscope.

These and other objects of the present invention will be apparent from a review of the following specification and the accompanying drawings.

BRIEF DESCRIPTION OF THE DRAWINGS

FIG. 1 is a side elevational view of an arthroscopic and cannula, with the arthroscope fully inserted.

FIG. 2 is a partial sectional side elevational view taken alone lines 3—3 of FIG. 1 of a cannula with an obdurator partially inserted.

FIG. 2a is a top partial view of the tip of the cannula.

FIG. 2b is a bottom partial view of the tip of the cannula.

FIG. 3 is a cross-sectional view of the proximal end fitting of the cannula.

FIG. 4 is a cross-sectional view taken along the lines 4—4 of FIG. 2 illustrating the invention using a corrugated construction.

FIG. 5 is a partial perspective view of the cannula constructed accordingly to the embodiment of FIG. 4.

FIG. 6 is a cross-sectional view of the cannula in which the cannula is constructed in a unitary form.

FIG. 6a is a cross-sectional end view of the cannula in which the cannula is oval.

FIG. 7 is a perspective view of a second alternative embodiment of the cannula, constructed with dimpled, radially inward projections.

FIG. 8 is a cross sectional view of the second alternative embodiment viewed along lines 8—8 of FIG. 7.

DETAILED DESCRIPTION OF THE DRAWINGS

Referring to FIGS. 1 and 3 there is shown a cannula 10 constructed in accordance with the present invention. FIG. 1 shows the arthroscope 38 coupled to the cannula 10 while FIG. 3 shows the obdurator 36 partially inserted in the cannula 10. The arthroscope 38 is of standard design and construction with the usual input light connection 40 and viewing eyepiece 42 typically connected to a television camera (not shown).

The cannula 10 consists of an elongated hollow tubular member 12 having a viewing end 15 and a distal end 13. The distal end 13 is beveled and slotted 17 to enable the arthroscope 38, which also has a beveled end, to have a clear field of view during use.

Proximate the viewing end 15 of the cannula 10 a bypass fitting 16 is provided which includes a collar 18 mounting opposed nipples 20, 22. Each fitting includes an in-line valve 24, 26 for selective closure and fittings 28, 30 for attachment to fluid carrying hoses (not shown).

The viewing end 15 of the cannula opens into a conical coupling member 32, shown in FIG. 3, having a sleeve 34 with an internal bayonet locking assembly 35 that engages projections in the end of the inserted instrument, such as an obdurator 36 or arthroscope 38.

An obdurator 36 is a solid member having an outside diameter approximately the same as the outside diameter of the arthroscope to be used, and is sufficiently long so that its distal end 120, when inserted in the cannula 10, extends beyond the distal end 13 of the cannula 10. The obdurator 36 has an enlarged opposite end 12b for ease of grasping.

Referring to FIG. 4 the internal structure of the tubular member 12 is shown supporting an arthroscopic element 38. The inside of the tubular member 12 has a plurality of longitudinal support segments 44, 46, 48, and 50 of uniform cross-section, projecting radially inwardly from the inner cannula wall 49 to just touch the arthroscopic viewing element 38. Enlarged spaces 51, 53, 55 and 57 are created between the outside wall of the arthroscopic element 38 and the inner wall 49 of the cannula. The support segments 44, 46, 48 and 50 are formed by corrugating the tubular member 12.

While specific dimensions will be given they should be taken in a proportional sense as the instrument may be scaled to different sizes as required. Accordingly, by way of example, a prior art arthroscopic cannula for a 4 mm arthroscope element has an outside diameter of 5.5 mm with a wall thickness of 0.5 mm and an inside diameter of about 4.5 mm. The approximate cross sectional flow area is about 3.32 mm$^2$. If the outside diameter is increased by 1 mm to 6.5 mm and the wall thickness is reduced to 0.4 mm, the cross sectional flow area is, compensating for the area of the support segments, approximately 10.89 mm$^2$, an increase of over 300% in the volumative space previously available.

The use of the corrugated support segments allows the use of a decreased wall thickness without compromising the support and protection afforded to the arthroscope for the following reasons: Firstly, as the diameter of a tube, assuming constant wall thickness, increases the resistance to bending increases; Secondly, the support segments themselves increase resistance to bending; and thirdly, since the support segments can be closer to the arthroscope, the force applied to the cannula to cause bending is uniformly transmitted, much as occurs with the spokes of a bicycle wheel, reducing breakage of the cannula.

While the preferred number of support segments for supporting the arthroscope is three, more may be used to provide stable support to the arthroscope. Further, if the ends of the support segments are concave so as to conform to the shape of the arthroscope element, as few as two support segments may be used to provide sufficient stability to the arthroscope.

Further, while in the preferred embodiment the cannula is tubular, it may have other cross sections, such as an oval as shown in FIG. 6a. In such a case, the arthroscope would be supported by two support segments extending from the narrow dimension of the oval. Fluid would flow in the large outer portions of the oval, on either side of the arthroscope.

The supporting segments can be of various constructions. Alternative embodiments of the invention are illustrated in FIGS. 6–8. In FIG. 6, a plurality of longitudinal support flutes 56, 58 and 60 are formed integrally with the cannula wall. These can be formed by conventional extrusion procedures.

FIG. 7 illustrates another embodiment of the cannula of the present invention having a plurality of inwardly spaced projecting dimples formed in the tubular member 12. The dimples may be either uniformly or randomly spaced to support the arthroscope. The cross section of the dimpled configuration is shown in FIG. 8. The dimples are preferably as steep as possible to increase the available flow area.

The device of the present invention is used in the same manner as a conventional cannula and arthroscope. An incision is made and the obdurator 36 is inserted into the cannula 10. The obdurator 36 projects slightly beyond the distal end of the cannula 10 and pushes through the soft tissue, gaining entrance for the cannula 10. Once inserted in place, the obdurator 36 is removed, leaving the cannula in place. The arthroscope 36 is then introduced into the cannula 10 and locked in place. The tubing is then attached to the inlet 28 and outlet 30. As a result of the larger volumetric space created in the cannula, there is increased capacity for the inflow and outflow of fluids.

While the above invention has been described with regards to its use with an arthroscope, it is recognized that the present inventive concept could be used with endoscope devices in general. Also, it is appreciated that variations of the construction of the cannula and the means of forming the projections can be made without departing from the present inventive concept disclosed.

What is claimed is:

1. A cannula for use with an endoscope surgical instrument comprising
a hollow tubular member having an inner and outer wall for surrounding an endoscope element said cannula having a plurality of separate support segments extending inwardly from said inner wall for supporting the endoscope element said support segments defining an open space between adjacent support segments and the interior of said hollow tubular member and attachment means at one end of said tubular member for attachment of said tubular member to a source of fluid and suction.

2. The device of claim 1 in which said hollow tubular member has a circular cross section.

3. The device of claim 1 in which said tubular member is corrugated.

4. The device of claim 1 in which said support segments are uniformly distributed.

5. The device of claim 1 in which said support segments comprise a plurality of spaced dimples extending inwardly into close fitting relation with the outer wall of an endoscope.

6. The devise of claim 5 in which said dimples are uniformly distributed within said tubular member.

7. The device of claim 1 in which said support segments are formed integrally with said tubular member.

8. The device of claim 1 in which said tubular member has an oval cross section.

9. An endoscope comprising of the combination of a hollow cannula for use with an arthroscope of the type including an arthroscope viewing element and a cannula for housing and protecting said arthroscope
said cannula having arthroscope supporting means extending inwardly from the inside wall of said cannula, said supporting means having a length greater than the thickness of the wall of said cannula said cannula having connecting means at one end for connecting said cannula to a source of fluid and suction.

10. The cannula of claim 9 in which said device is corrugated.

11. The device of claim 9 in which the space between the wall of said cannula and the outside wall of the arthroscope is not uniform.

12. The device of claim 9 in which there are at least three separate supporting means for supporting said arthroscope.

13. The device of claim 9 in which the inside diameter of said cannula is approximately 5.7 mm and the outside diameter of the arthroscope is approximately 4.0 mm.

14. The device of claim 9 in which said cannula has a non circular cross section.

15. The device of claim 9 in which the cross sectional area between the inside wall of said cannula and the outside diameter of said arthroscope is more than 5 mm$^2$.

* * * * *